(12) United States Patent
Gijsen et al.

(10) Patent No.: US 8,461,145 B2
(45) Date of Patent: Jun. 11, 2013

(54) DIBENZOAZEPINE AND DIBENZOOXAZEPINE TRPA1 AGONISTS

(75) Inventors: Henricus Jacobus Maria Gijsen, Breda (BE); Marc Hubert Mercken, Turnhout (BE)

(73) Assignee: Janssen Pharmaceutica NV, Beerse (BE)

( * ) Notice: Subject to any disclaimer, the term of this patent is extended or adjusted under 35 U.S.C. 154(b) by 304 days.

(21) Appl. No.: 12/746,092

(22) PCT Filed: Dec. 4, 2008

(86) PCT No.: PCT/EP2008/066813
§ 371 (c)(1),
(2), (4) Date: Jun. 3, 2010

(87) PCT Pub. No.: WO2009/071631
PCT Pub. Date: Jun. 11, 2009

(65) Prior Publication Data
US 2010/0273773 A1 Oct. 28, 2010

(30) Foreign Application Priority Data

Dec. 5, 2007 (EP) .................................. 07122339
May 29, 2008 (EP) .................................. 08157200

(51) Int. Cl.
*A61K 31/55* (2006.01)
*A61K 31/553* (2006.01)
*C07D 233/20* (2006.01)
*C07D 267/20* (2006.01)
*A61P 25/00* (2006.01)

(52) U.S. Cl.
USPC ....... 514/211.11; 514/217; 540/547; 540/587

(58) Field of Classification Search
USPC ...................... 514/211.11, 217; 540/547, 587
See application file for complete search history.

(56) References Cited

U.S. PATENT DOCUMENTS 4,263,207 A 4/1981 Rokach et al.

FOREIGN PATENT DOCUMENTS

| EP | 0 040 860 A1 | 12/1981 |
| EP | 0 040 860 B1 | 12/1981 |
| WO | WO 2004 026030 A2 | 4/2004 |
| WO | WO 2005 089206 A2 | 9/2005 |
| WO | WO 2007 073505 A2 | 6/2007 |
| WO | WO 2007 098252 A2 | 8/2007 |

OTHER PUBLICATIONS

International Search Report for Corresponding International Application No. WO2009/071631 Dated Sep. 17, 2009 3 Pgs.

Akopian et al "Transient Receptor Potential TRPA1 Channel Desensitization in Sensory Neurons is Agonist Dependent and Regulated by TRPV1-Directed Internalization" J Phys 2007 vol. 583 (Pt 1) pp. 175-193.
Andrade et al "Contractile Mechanisms Coupled to TRPA1 Receptor Activation in Rat Urinary Bladder" Biochem Pharmacol 2006 vol. 72 pp. 104-114.
Levine et al "TRP Channels: Targets for the Relief of Pain" Biochimica Et Biophysica Acta 2007 vol. 1772 pp. 989-1003.
Blain et al "Tear Gases and Irritant Incapacitants. 1-Chloroacetophenone, 2-Chlorobenzylidene Malononitrile and Dibenz[B,F]-1,4-Oxazepine" Toxicol Rev 2003 vol. 22 pp. 103-110.
Bley et al "Recent Developments in Transient Receptor Potential Vanilloid Receptor 1 Agonist-Based Therapies" Expert Opin Investig Drugs 2004 vol. 13(11) pp. 1445-1456.
Bautista et al "TRPA1 Mediates the Inflammatory Actions of Environmental Irritants and Proalgesic Agents" Cell 2006 vol. 124 pp. 1269-1282.
McMahon et al "Increasingly Irritable and Close to Tears: TRPA1 in Inflammatory Pain" Cell 2006 vol. 124 pp. 1123-1125.
Penuelas et al. "Contractile Effect of TRPA1 Receptor Agonists in the Isolated Mouse Intestine" European Journal of Pharmacology 2007 vol. 576 pp. 143-150.
Maruyama et al "Influence of Local Treatments With Capsaicin or Allyl Isothiocyanate in the Sensitization Phase of a Fluorescein-Isothiocyanate-Induced Contact Sensitivity Model" International Archives of Allergy and Immunology 2007 vol. 143(2) pp. 144-154.
Nagarajan et al "Dibenzoxazepines—Chemistry and Biological Activity" Studies in Organic Chemistry 1979 vol. 3 pp. 317-340.
Olajos et al "Riot Control Agents: Pharmacology, Toxicology, Biochemistry and Chemistry " Appl Toxicol 2001 vol. 21 pp. 355-391.
Trevisani et al "4-Hydroxynonenal, an Endogenous Aldehyde, Causes Pain and Neurogenic Inflammation Through Activation of the Irritant Receptor TRPA1" PNAS 2007 vol. 103 pp. 13519-13524.
Wardrop et al "Preparation of -Some Dibenz[B,F] [1 ,4]Oxazepines and Dibenz[B,E]Azepines" J Chem Soc Perkin Trans I. 1976 pp. 1279-1285.

*Primary Examiner* — Brenda Coleman
(74) *Attorney, Agent, or Firm* — Michael J. Atkins

(57) ABSTRACT

The present invention is related to novel tricyclic compounds of formula (I) having TRPA1 receptor agonistic properties, pharmaceutical compositions comprising these compounds, chemical processes for preparing these compounds and their use as pharmacological tools, or as irritant incapacitants, or in the treatment of diseases linked to the modulation of the TRPA1 receptors in animals, in particular humans.

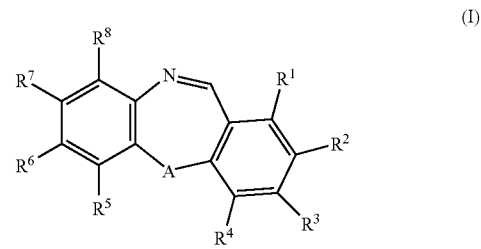

(I)

11 Claims, No Drawings

DIBENZOAZEPINE AND DIBENZOOXAZEPINE TRPA1 AGONISTS

CROSS-REFERENCE TO RELATED APPLICATIONS

This application is a national phase of International Application No. PCT/EP2008/066813 filed on Dec. 04, 2008, which application claims priority from EP 07122339.0 filed on Dec. 05 2007, and EP 08157200.0 filed on May 29, 2008.

The present invention is related to novel tricyclic compounds of formula (I) having TRPA1 receptor agonistic properties, pharmaceutical compositions comprising these compounds, chemical processes for preparing these compounds and their use as pharmacological tools, or as irritant incapacitants, or in the treatment of diseases linked to the modulation of the TRPA1 receptors in animals, in particular humans.

The Transient Receptor Potential A1 (TRPA1), formerly named ANKTM1, receptor belongs to the transient receptor potential (TRP) family of cation-selective channels which have been shown to transduce mechanical, thermal, and pain-related inflammatory signals (see e.g. Biochimica et Biophysica Acta 1772 (2007) 989-1003; Cell 124 (2006) 1123-1125).

TRPA1 is a non-selective calcium permeable channel, modulating membrane potential by modulating the flux of cations such as calcium and sodium ions. The miss-regulation of ion channels is often associated with pathological conditions, and compounds, which are able to modulate one or more functions of ion-channels, including TRPA1, are of great interest as possible therapeutic agents. Activators or agonists of the TRPA1 receptor, such as isothiocyanates (allylisothiocyanate, the pungent component of mustard), cause acute pain and neurogenic inflammation. (see e.g. PNAS 103 (2007) 13519-13524; Cell 124 (2006) 1269-1282).

Another member of this family of ion channels is the TRPV1 receptor. It has been shown that activation of this receptor leads to desensitization of the receptor and hence analgesic activity (See Bley, K. R. Expert Opin. Investig. Drugs. 2004 13(11), 1445-1456). Modulation of the TRPA1 receptor may likewise lead to an improved homeostasis of ion-flux and membrane potential. Desensitization of the TRPA1 receptor by the known agonists allylisothicyanate and cinnamaldehyde has been demonstrated (See Andrade, E. L, Biochem. Pharmacol. 2006, 72, 104-114, Akopian, A. N. J. Phys. 2007, 583(Pt 1), 175-193). Local pretreatment of mice with the TRPA1 agonist allylisothiocyanate reduced contact hypersensitivity towards fluorescein isothiocyanate (FITC) as shown by a reduction in the ear swelling response (See International Archives of Allergy and Immunology (2007), 143(2), 144-154). Activation of the TRPA1 receptor has also shown to result in contraction of the rat urinary bladder (Andrade, E. L, Biochem. Pharmacol. 2006, 72, 104-114) and the mouse intestine (European Journal of Pharmacology (2007), 576, 143-150).

There is an interest in the identification and development of ligands to the TRPA1 receptor to be of possible use in the prevention, treatment, or alleviating symptoms of a disease or condition associated with TRPA1 (see for example WO-2007/073505 or WO-2007/098252 for patents claiming TRPA1 antagonists). The TRPA1 agonistic compounds of the present invention—with a potency exceeding the currently described agonists used for screening purposes such as allyl- or benzylisothiocyanate—can be used as an agent in a screening assay for identifying TRPA1 antagonists, or determination of their affinity and potency. In addition to the increased potency over the currently used agonists such as allyl- or benzyliosthiocyanate, the TRPA1 agonistic compounds of the present invention have an additional advantage over these known compounds due to their lower sensitivity to other nucleophilic agents present in the assay, making the resulting signal more stable.

Dibenz[b,f][1,4]oxazepine (military code CR) is a known riot control agent with powerful lacrimatory and skin irritating properties. It is of particular interest as a riot control agent due to its lower toxicity than some other commonly used riot control agents such as CN (chloroacetophenone) (see e.g. Blain, P. G. Toxicol. Rev. 2003, 22, 103-110: Tear gasses and Irritant Incapacitants; Olajos, E. J.; Salem, H. J. Appl. Toxicol. 2001, 21, 355-391. Apart from CR, corresponding dibenz [b,e]azepines (morphanthridines) and dibenz[b,f][1,4]thiazepines have also been described as irritating compounds (see e.g. Wardrop, A. W. H.; Sainsbury, G. L.; Harrison, J. M.; Inch, T. D. J. Chem. Soc, Perkin. Trans. I. 1976, 1279-1285 and refs 1 and 2 in this article). A disadvantage of the use of CR is the persistence in the environment due to it's stability in aqueous media. CR has been shown (in-house data) to be a potent activator of the TRPA1 receptor (pEC50 hTRPA1=9.5). Likewise acrolein, a known environmental irritant which has been used as a tear gas, has been shown to be an activator of the TRPA1 receptor (Cell, 2006, 124, 1269-1282).

The claimed compounds exhibit similar lacrimatory properties and skin irritating properties as CR, and could therefore be used as ingredients in tear gasses or riot control agents, also referred to as irritants, irritating agents, harassing agents and incapacitating agents or short-term incapacitants. In addition they may be more soluble and less stable in aqueous media, making them less persistent in the environment.

Dibenz[b,f][1,4]oxazepines with COOR substituents on $R^5$-$R^8$ have been described in EP-0,040,860-A which discloses dibenzoxazipine derivatives having lipid lowering activity, blood sugar lowering activity and activity to inhibit the aggregation of platelets. Tricyclic compounds, including dibenzoxazepines and morphanthridines containing electron withdrawing groups such as CN, $CF_3$, and $NO_2$, have been claimed in WO-2004/026030 as having insecticidal activity.

The claimed compounds have unexpectedly been shown to be activators of the human TRPA1 receptor.

The present invention relates to novel compounds of formula (I)

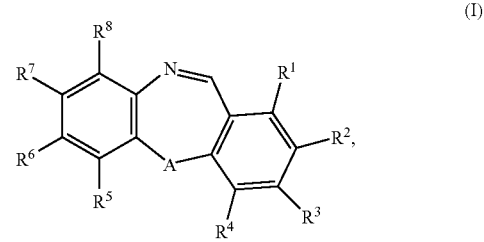

including any stereochemically isomeric form thereof wherein

A is $CH_2$, CO, or O;

$R^1$, $R^2$, $R^3$, $R^4$, $R^5$, $R^6$, $R^7$ and $R^8$ are each independently selected from hydrogen, halo, hydroxy, $C_{1-6}$alkyl, polyhalo$C_{1-6}$alkyl, $C_{3-6}$cycloalkyl, $C_{1-6}$alkyloxy, polyhalo$C_{1-6}$alkyloxy, $COOR^9$ or $CONR^{10}R^{11}$;

$R^9$, $R^{10}$ and $R^{11}$ are each independently selected from hydrogen, $C_{1-6}$alkyl, $C_{1-4}$alkyloxy$C_{1-4}$alkyl, polyhalo$C_{1-6}$alkyl, polyhalo$C_{1-4}$alkyloxy$C_{1-4}$alkyl, $C_{3-6}$cycloalkyl, $C_{3-6}$cycloalkyl$C_{1-4}$alkyl, amino$C_{2-5}$alkyl, mono- or (di$C_{1-4}$alkyl)amino$C_{2-5}$alkyl; and wherein $NR^{10}R^{11}$ may form a heterocyclic ring selected from pyrrolidine, piperidine, morpholine, piperazine, or piperazine substituted with $C_{1-4}$alkyl;

provided that at least least one of $R^1$ to $R^8$ is defined as $COOR^9$ or $CONR^{10}R^{11}$; and provided that when radical A represents O then the substituents $R^5$ to $R^8$ should not be $COOR^9$;

or a pharmaceutically acceptable acid addition salt thereof, or a solvate thereof, or an N-oxide thereof.

The proviso is intended to exclude the compounds described in EP-0,040,860-A which discloses dibenzoxazipine derivatives having lipid lowering activity, blood sugar lowering activity and activity to inhibit the aggregation of platelets.

As used in the foregoing definitions:

halo is generic to fluoro, chloro, bromo and iodo;

$C_{1-4}$alkyl defines straight and branched chain saturated hydrocarbon radicals having from 1 to 4 carbon atoms such as, for example, methyl, ethyl, propyl, butyl, 1-methyl-ethyl, 2-methylpropyl and the like;

$C_{2-5}$alkyl defines straight and branched chain saturated hydrocarbon radicals having from 2 to 5 carbon atoms such as, for example, ethyl, propyl, butyl, 1-methylethyl, 2-methylpropyl, 2-methylbutyl, pentyl and the like;

$C_{1-6}$alkyl is meant to include $C_{1-4}$alkyl and the higher homologues thereof having 5 or 6 carbon atoms, such as, for example, 2-methylbutyl, pentyl, hexyl and the like;

polyhalo$C_{1-4}$alkyl is defined as polyhalosubstituted $C_{1-4}$alkyl, in particular $C_{1-4}$alkyl (as hereinabove defined) substituted with 2 to 6 halogen atoms such as difluoromethyl, trifluoromethyl, trifluoroethyl, and the like;

$C_{3-6}$cycloalkyl is generic to cyclopropyl, cyclobutyl, cyclopentyl, and cyclohexyl.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Stereochemically isomeric forms of the compounds of formula (I) are obviously intended to be embraced within the scope of this invention.

The absolute stereochemical configuration of the compounds of formula (I) and of the intermediates used in their preparation may easily be determined by those skilled in the art while using well-known methods such as, for example, X-ray diffraction.

Furthermore, some compounds of formula (I) and some of the intermediates used in their preparation may exhibit polymorphism. It is to be understood that the present invention encompasses any polymorphic forms possessing properties useful in the treatment of the conditions noted hereinabove.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) may exist in both unsolvated and solvated forms. The term 'solvate' is used herein to describe a molecular association comprising a compound of the invention and one or more pharmaceutically acceptable solvent molecules, e.g. water or ethanol. The term 'hydrate' is used when said solvent is water.

Preferably: one of the substituents $R^1$ to $R^8$ is $COOR^9$, wherein $R^9$ is $C_{1-4}$alkyl or $CONH_2$.

More preferably: one of the substituents $R^1$ to $R^8$ is $COOR^9$, wherein $R^9$ is $C_{1-4}$alkyl or $CONH_2$, and the other $R^1$ to $R^8$ substituents are hydrogen and A is $CH_2$, CO or O.

Most preferably: substituent $R^4$ is $COOR^9$ wherein $R^9$ is $C_{1-4}$alkyl or $CONH_2$, and the other substituents $R^1$, $R^2$, $R^3$, $R^5$, $R^6$, $R^7$ and $R^8$ are hydrogen and A is $CH_2$ or O, or $R^6$ is $COOR^9$ wherein $R^9$ is $C_{1-4}$alkyl, and the substituents $R^1$, $R^2$, $R^3$, $R^4$, $R^5$, $R^7$ and $R^8$ are hydrogen and A is $CH_2$, or $R^5$ is $COOR^9$ wherein $R^9$ is $C_{1-4}$alkyl, and the substituents $R^1$, $R^2$, $R^3$, $R^4$, $R^6$, $R^7$ and $R^8$ are hydrogen and A is $CH_2$.

General Synthesis (Synthetic Routes)

The synthesis of (substituted) tricyclic compounds of general structure I (A=O) has been reviewed (Nagarajan, K. *Studies in Organic Chemistry,* 1979, 3, 317-340).

Analogously, the corresponding dibenzo[b,e]azepines can be prepared (See for example Wardrop, A. *J. Chem. Soc. Perkin Trans.* 1, 1976, 1279).

Introduction of the carboxylic acid ester or amide substituent was found to be most convenient at the dihydro intermediates (II) of the desired compounds, followed by final oxidation to the desired compounds (I). Oxidation of the $CH_2NH$ bond in intermediates of formula (II) to the $CH{=}N$ bond can be accomplished by prolonged (weeks to months) exposure of a suitable solution of an intermediate (II) (in e.g. DMSO) to air, or by heating of an intermediate (II) in the presence of sulphur, or treatment of an intermediate of formula (II) with palladium catalyst, or another oxidizing agent such as manganese oxide ($MnO_2$) in a suitable solvent such as xylene or toluene, at temperatures varying from room temperature to reflux.

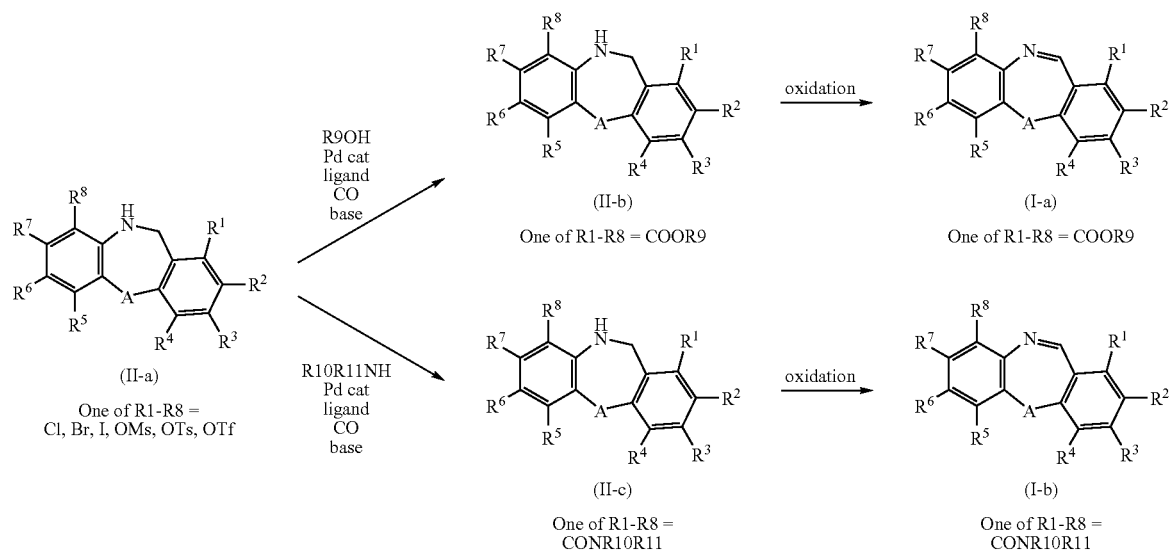

Compounds (1-b), defined as compounds of formula (I) wherein $R^{10}=R^{11}=$hydrogen, can also be obtained by treatment of a compound (II-a), defined as a compound of formula (I) wherein one of $R^1$-$R^8$=CN, with sulfuric acid, followed again by an oxidation method as described above for the synthesis of compound (1-b). Intermediates (II-c) can also be obtained by conversion of the ester functionality in (II-b) or its corresponding acids (R9=H) into an amide functionality.

Dihydro-dibenzo[b,e]azepines compounds of formula (II-d), defined as compounds of formula (II-a) wherein A is $CH_2$, can be prepared by treatment of intermediate (VI) with sulfuric acid. Intermediate (VI) can be prepared via condensation of intermediate (III) with aldehyde (IV), followed by reduction of the resulting intermediate (V).

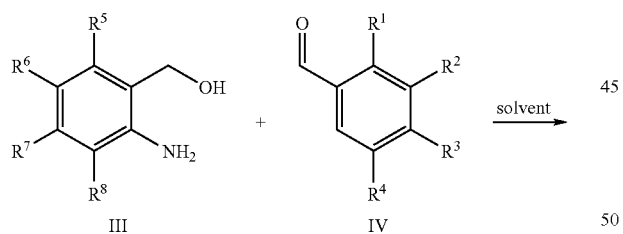

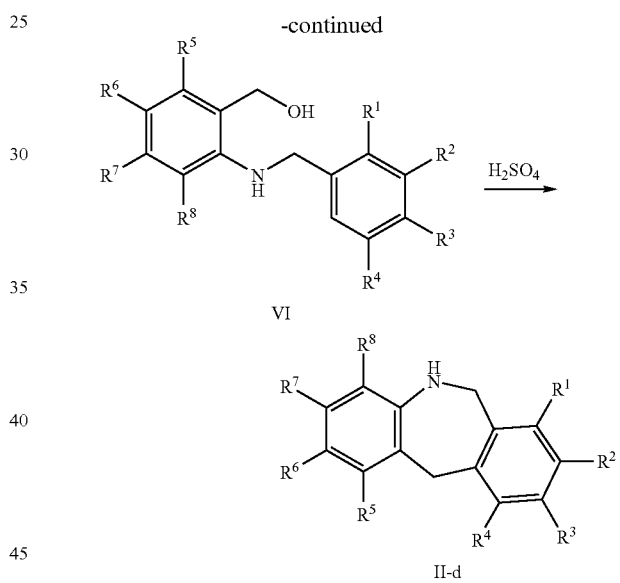

Dihydro-dibenzo[b,f][1,4]oxazepine compounds of formula (II-e), defined as compounds of formula (II-a) wherein A is O, can be prepared starting form amide formation between aniline (VII) and acid chloride (VIII), or a corresponding activated carboxylic acid derivative, wherein X=halo, to give intermediate (IX). Intermediate (IX) can be cyclized to be cyclized to intermediate (X), which can subsequently be reduced to compound (II-e):

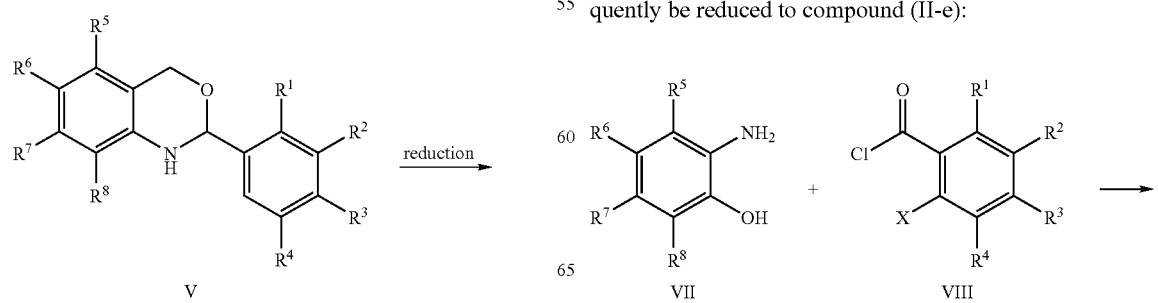

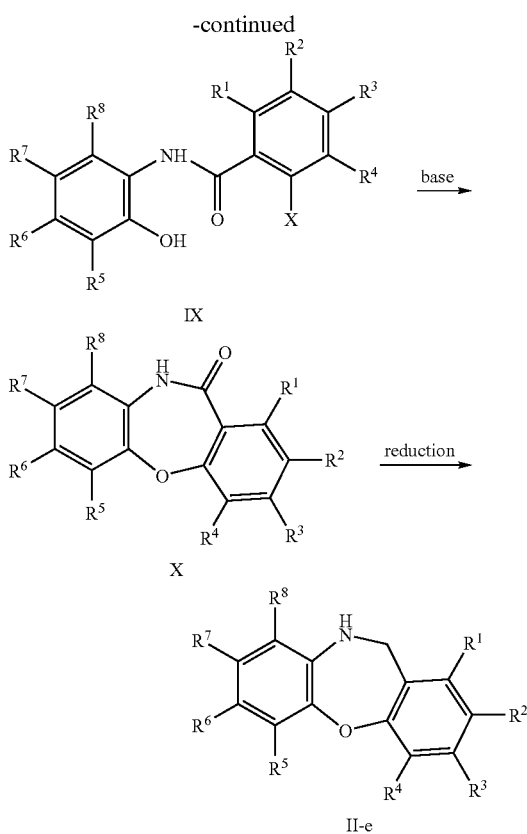

The starting materials and some of the intermediates are known compounds and are commercially available or may be prepared according to conventional reaction procedures generally known in the art.

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the pharmaceutically acceptable salts and stereoisomeric forms thereof possess transient receptor potential A1 receptor (TRPA1) agonistic properties as demonstrated in the Pharmacological Examples. Pharmacological example D.1 describes the methodology to measure TRPA1 agonism and results are listed in Table 3.

Therefore the present compounds of formula (I) are useful as a medicine especially in the treatment of a condition or disease mediated by the TRPA1 receptor, in particular TRPA1 receptor agonistic activity. Subsequently the present compounds may be used for the manufacture of a medicine for treatment of a condition or a disease mediated by TRPA1 activity, in particular TRPA1 agonistic activity.

Preferably, the present invention also provides the use of a compound of formula (I) or a pharmaceutically acceptable salt thereof for the manufacture of a medicament for the treatment of conditions or diseases selected from TRPA1 mediated conditions or diseases.

Further, the present invention provides a method of treatment of a condition mediated by TRPA1 activity, in a mammalian subject, which comprises administering to a mammal in need of such treatment a therapeutically effective amount of a compound of formula (I) or a pharmaceutically acceptable salt thereof.

TRPA1 mediated conditions or diseases are e.g. pain, chronic pain, touch sensitivity, itching sensitivity, skin irritation, post-surgical pain, cancer pain, neuropathic pain, inflammatory pain, migraine, urinary incontinence, inhibition or stimulation of hair growth, lacrimation, ocular injuries, blepharospasm, and pulmonary irritation.

Furthermore, due to their lacrimatory properties and skin irritating properties TRPA1 agonists in general, and the compounds of the present invention in particular, can also be used as an agent for riot control, animal pest control, and for self defence.

The term "treating" and "treatment', as used herein, refers to curative, palliative and prophylactic treatment, including reversing, alleviating, inhibiting the progress of, or preventing the disease, disorder or condition to which such term applies, or one or more symptoms of such disease, disorder or condition.

Additionally the present invention provides pharmaceutical compositions comprising at least one pharmaceutically acceptable carrier and a therapeutically effective amount of a compound of formula (I).

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1',6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of formula (I) may also be formulated in rectal compositions such as suppositories or retention enemas, e.g. containing conventional suppository bases such as cocoa butter and/or other glycerides.

Those of skill in the treatment of diseases linked to the mediation of the TRPA1 receptor will easily determine the therapeutically effective amount of a compound of formula (I) from the test results presented hereinafter. In general it is contemplated that a therapeutically effective dose will be from about 0.001 mg/kg to about 50 mg/kg of body weight, more preferably from about 0.01 mg/kg to about 10 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 1000 mg, more particularly from about 1 to about 500 mg, of the active ingredient per unit dosage form.

As used herein, a "therapeutically effective amount" of a compound, is the quantity of a compound which, when administered to an individual or animal, results in a sufficiently high level of that compound in the individual or animal to cause a discernible increase or decrease in stimulation of TRPA1 receptors.

The exact dosage and frequency of administration depends on the particular compound of formula (I) used, the particular condition being treated, the severity of the condition being treated, the age, weight and general physical condition of the particular patient as well as the other medication, the patient may be taking, as is well known to those skilled in the art. Furthermore, said "therapeutically effective amount" may be lowered or increased depending on the response of the treated patient and/or depending on the evaluation of the physician prescribing the compounds of the instant invention. The effective daily amount ranges mentioned hereinabove are therefore only guidelines.

EXPERIMENTAL PART

"DIPE" is defined as diisopropyl ether, "DMF" is defined as N,N-dimethylformamide, "DMSO" is defined as dimethyl sulfoxide, "DCM" is defined as dichloromethane, "EtOAc" is defined as ethyl acetate, "MeOH" is defined as methanol, "EtOH" is defined as ethanol and "THF" is defined as tetrahydrofuran.

High-Performance Liquid Chromatography Purification Methods:

Purification Method A

The product was purified by reversed phase high-performance liquid chromatography (Shandon Hyperprep® C18 BDS (Base Deactivated Silica) 8 μm, 250 g, I.D. 5 cm). A gradient with three mobile phases was applied (phase A: a 0.25% $NH_4HCO_3$ solution in water; phase B: $CH_3OH$; phase C: $CH_3CN$). The desired fractions were collected and worked-up.

Purification Method B

The product was purified by reversed phase high-performance liquid chromatography (Shandon Hyperprep® C18 BDS (Base Deactivated Silica) 8 μm, 250 g, I.D. 5 cm). A gradient with three mobile phases was applied (phase A: 90% of a 0.5% $NH_4OAc$ solution in water+10% $CH_3CN$; phase B: $CH_3OH$; phase C: $CH_3CN$). The desired fractions were collected and worked-up.

Purification Method C

The product was purified by reversed phase high-performance liquid chromatography (Shandon Hyperprep® C18 BDS (Base Deactivated Silica) 8 μm, 250 g, I.D. 5 cm). A gradient with two mobile phases was applied (phase A: a 0.25% $NH_4HCO_3$ solution in water; phase B: $CH_3CN$). The desired fractions were collected and worked-up.

A. Synthesis of the Intermediates

Example A.1 a) Preparation of

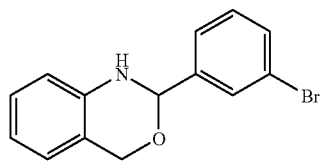

intermediate (1)

A mixture of 2-amino-benzenemethanol (0.073 mol) and 3-bromo-benzaldehyde (0.073 mol) in 2-propanol (100 mL) was stirred for 3 hours at room temperature. The solvent was evaporated. Part (3 g) of the residue (20.5 g) was crystallized from hexane. The precipitate was filtered off and dried, yielding 1.37 g of intermediate (1).

b) Preparation of

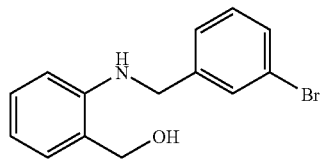

intermediate (2)

Reaction under nitrogen atmosphere. Sodium borohydride (0.1172 mol) was added slowly to a mixture of intermediate (1) (0.0586 mol) in ethanol (200 mL). The reaction mixture was stirred and refluxed for 1 hour. The mixture was cooled on an ice-water bath, quenched with $NH_4Cl$ 20% and extracted with $CH_2Cl_2$. The organic layer was dried, filtered and the solvent was evaporated, yielding 14.8 g of intermediate (2).

c) Preparation of

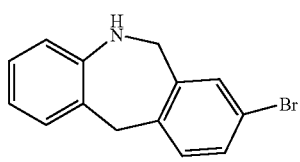

intermediate (3)

and

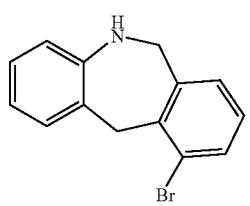

intermediate (4)

A solution of intermediate (2) (0.180 mol) in $CH_2Cl_2$ (50 mL) was added over a one-hour period to a cooled (±−10 to −20° C.) solution of concentrated $H_2SO_4$ (500 mL). Then the ice-bath was removed, and the mixture was stirred for one hour at room temperature. The reaction mixture was added to ice-water, cooled on ice, and alkalized with a 50% aqueous NaOH solution. The resulting mixture (±3 L) was extracted with $CH_2Cl_2$. The organic layer was separated, dried on $MgSO_4$, filtered and the filtrate was concentrated in vacuo. A part (8 g) of this residue was purified via Supercritical Fluid Chromatography (SFC, column: Diacel AD-H 30×250 mm, mobile phase: 55% MeOH/45% $CO_2$+0.2% isopropylamine, 40° C., 100 bar) to give 2 g of intermediate (4) (7-bromo-isomer) and 4.65 g of intermediate (3) (9-bromo-isomer).

d) Preparation of

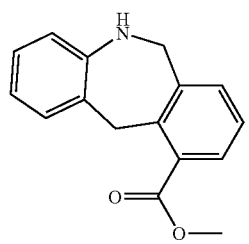

intermediate (5)

A mixture of intermediate (4) (0.008 mol), potassium acetate (4 g), $Pd(OAc)_2$ (0.04 g) and 1,1'-(1,3-propanediyl)bis[1,1-d]phenyl-phosphine (0.16 g) in methanol (100 mL) and THF (100 mL) was placed in a pressure reactor and pressurized with CO gas up to 50 kg/square cm. The reaction mixture was heated at 125° C. for 16 hours, then cooled, filtered over dicalite, and the solvent was evaporated. The residue was partitioned between $CH_2Cl_2$ and water. The organic layer was dried over $MgSO_4$, filtered, then the filtrate was concentrated. The residue was purified by column chromatography over silica gel (eluent: $CH_2Cl_2$). The desired fractions were collected and the solvent was evaporated, yielding 1.86 g of intermediate (5).

Using an analogous procedure as described in steps a), b), c), and d) intermediate (21) was prepared starting from 4-bromo-benzaldehyde.

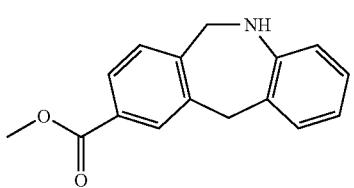

intermediate (21)

Using an analogous procedure as described in step d) intermediate (23) was prepared starting from intermediate (3) and 2-propanol.

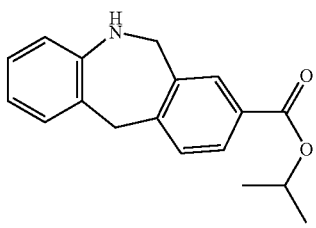

intermediate (23)

Example A.2 a) Preparation of

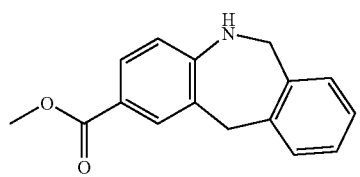

intermediate (6)

A mixture of 2-bromo-6,11-dihydro-5H-dibenz[b,e]azepine (0.05 mol), potassium acetate (0.1 mol), Pd(OAc)$_2$ (0.112 g) and 1,1'-(1,3-propanediyl)bis[1,1-d]phenyl-phosphine (0.412 g) in methanol (150 mL) was placed in a pressure reactor and pressurized with CO gas up to 50 kg/square cm. The reaction mixture was heated at 150° C. for 24 hours, then cooled and the solvent was evaporated. The residue was partitioned between NH$_4$OH/H$_2$O and CH$_2$Cl$_2$. The organic layer was separated, dried, filtered and the solvent was evaporated. The residue was triturated under DIPE, filtered off and dried (vacuum, 40° C.), yielding 10.5 g of intermediate (6).

b) Preparation of

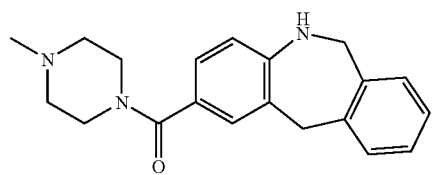

intermediate (7)

A solution of 1-methyl-piperazine (0.01496 mol) in CH$_2$Cl$_2$ (dried, 20 mL) was stirred at 0° C. under nitrogen atmosphere. Chlorodimethylaluminum 1M in hexane (0.01496 mol) was added dropwise and the resulting mixture was warmed to room temperature and stirred for 15 minutes. A solution of intermediate (6) (0.00748 mol) in CH$_2$Cl$_2$ (dried, 20 mL) was added and the resulting reaction mixture was stirred and refluxed for 2 days. Then, the reaction mixture was cooled to 0° C. and a 20% NH$_4$Cl solution was added carefully. The organic layer was washed and an emulsion formed, which was filtered through dicalite. The organic layer was dried and evaporated under reduced pressure. The residue was redissolved in CH$_2$Cl$_2$ and washed with 3 N HCl. The aqueous layer was washed 2× with CH$_2$Cl$_2$ and alkalized with 20% NaOH. This mixture was extracted with CH$_2$Cl$_2$. The separated organic layer was dried, filtered and the solvent was evaporated under vacuum. The residue was purified by HPLC over silica gel (eluent: CH$_2$Cl$_2$/CH$_3$OH 95/5 up to 90/10). The desired fractions were collected and the solvent was evaporated, yielding 0.18220 g of intermediate (7), melting point. 138.3° C.

Using an analogous procedure as described in step b) intermediate (22) was prepared starting from intermediate (21).

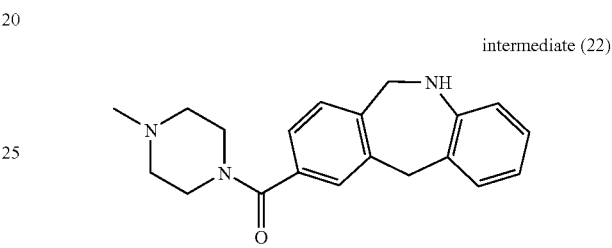

intermediate (22)

Example A.3 a) Preparation of

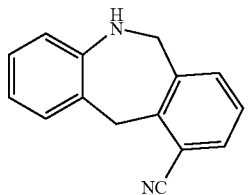

intermediate (8)

A mixture of intermediate (4) (0.0029 mol) and copper cyanide (0.0073 mol) in DMF (15 mL) was degassed and then shaken under nitrogen atmosphere at 140° C. for 3 days.

The reaction mixture was cooled. NaOH (200 mL, 0.2N) was added. This mixture was extracted 2× with 100 mL of ethyl acetate. The organic layer was separated, washed with water and brine, dried over MgSO$_4$, filtered and the filtrate's solvent was evaporated. The residue was purified over a silica gel filter (eluent: CH$_2$Cl$_2$). The product fractions were collected and the solvent was evaporated, yielding 0.53 g of intermediate (8).

b) Preparation of

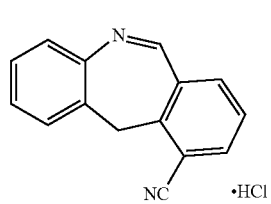

intermediate (9)

A mixture of intermediate (8) (0.0018 mol) and manganese oxide (0.009 mol) in toluene (15 mL) was stirred at 90° C. for 4 hours. The reaction mixture was filtered over a dicalite pad and washed with CH$_2$Cl$_2$. The organic layer was evaporated. The residue was dissolved in diethyl ether and 2 mL of 1N HCl in diethyl ether was added. The precipitate was filtered off, washed with diethyl ether and dried in vacuo, yielding 0.350 g of intermediate (9).

Example A.4 a) Preparation of

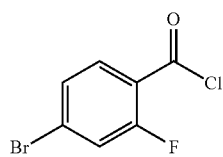

intermediate (10)

A mixture of 4-bromo-2-fluoro-benzoic acid (24 mmol) and thionyl chloride (20 mL) was refluxed for 2 hours. The reaction mixture was concentrated in vacuo and co-evaporated twice with toluene (40 mL), yielding intermediate (10). The residue was used as such in the next step.

b) Preparation of

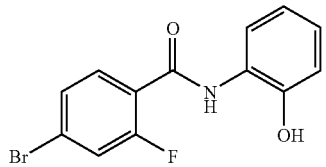

intermediate (11)

A mixture of intermediate (10) (24 mmol) in THF (25 mL) was added dropwise to a mixture of 2-amino-phenol (24 mmol) and triethylamine (48 mmol) in THF (75 mL) at 0° C. The reaction mixture was allowed to warm to room temperature and stirred overnight, then poured out into water (400 mL) and acidified to pH 4-5 with 1N aqueous HCl. The precipitate was filtered off and washed with 1 N HCl and water, dried in vacuo, yielding 6600 mg of intermediate (11).

c) Preparation of

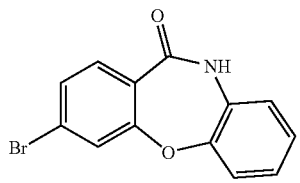

intermediate (12)

A mixture of intermediate (11) (20.96 mmol) and sodium hydroxide (20.96 mmol) in DMF (100 mL) was refluxed for 5 hours. The reaction mixture was poured onto 800 mL ice water and the resulting precipitate was filtered off and washed with 1N aqueous NaOH and water, then dried in vacuo, yielding 5600 mg of intermediate (12).

d) Preparation of

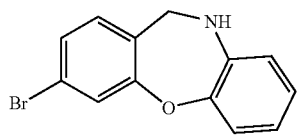

intermediate (13)

To a suspension of intermediate (12) (10.7 mmol) in THF (100 mL) was added borane-dimethyl sulfide complex (1:1) (2M in THF; 29.4 mmol) at room temperature. The reaction mixture was stirred further at room temperature for two days. The reaction mixture was cooled on ice and 100 mL 1N aq. HCl was added. The mixture was partly concentrated in vacuo, then alkalized with solid NaHCO$_3$ (pH about 7). The aqueous layer was extracted twice with 200 mL CH$_2$Cl$_2$. The organic layer dried on MgSO$_4$ and concentrated. The residue was purified by column chromatography over silica gel (eluent heptane/CH$_2$Cl$_2$ 70/30 to 20/80). The product fractions were collected and the solvent was evaporated, yielding 1700 mg of intermediate (13).

e) Preparation of

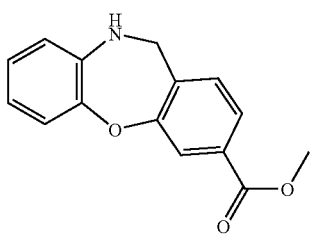

intermediate (14)

A 75-mL stainless steal autoclave was charged under nitrogen atmosphere with intermediate (13) (5.94 mmol), (Pd (OAc)$_2$ (10 mg), 1.3 bis(diphenylphosphino)-propane (40 mg), potassium acetate (1.5 g), methanol 20 mL) and THF (20 mL). The autoclave was closed and pressurized to 50 bar with carbonmonoxide and the reaction was carried out for 16 hours at a temperature of 125° C. The reaction mixture was filtered and concentrated in vacuo. The residue was partitioned between CH$_2$Cl$_2$ and water. The organic layer was dried on MgSO$_4$ and concentrated. The residue was purified by silica gel column chromatography (eluent CH$_2$Cl$_2$), yielding 1380 mg of intermediate (14).

Example A.5 a) Preparation of

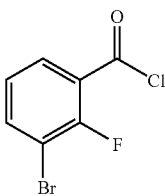

intermediate (15)

A mixture of 3-bromo-2-fluoro-benzoic acid (22 mmol) and thionyl chloride (20 mL) was stirred and refluxed for 2 hours. The reaction mixture was concentrated in vacuo, and co-evaporated twice with toluene (40 mL), yielding intermediate (15), which was used as such in the next step.

b) Preparation of

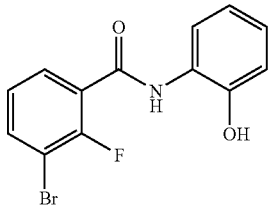
intermediate (16)

A mixture of intermediate (15) (22 mmol) in THF (25 mL) was added dropwise to a mixture of 2-amino-phenol (22 mmol) and triethylamine (44 mmol) in THF (75 mL) at 0° C. The reaction mixture was allowed to warm to room temperature and stirred overnight. The reaction mixture was poured into water (400 mL) and acidified to pH=4 to 5 with 1N aqueous HCl. The precipitate was filtered off and washed with 1N HCl and water, dried in vacuo, yielding 6350 mg of intermediate (16).

c) Preparation of

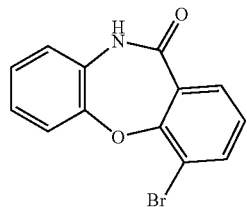
intermediate (17)

A mixture of intermediate (16) (20.5 mmol) and sodium hydroxide (powdered, 20.5 mmol) in DMF (100 mL) was stirred and refluxed for 5 hours. The reaction mixture was poured onto 800 mL ice water and the resulting precipitate filtered off and washed with 1N aqueous sodium hydroxide and water, then dried in vacuo, yielding 5200 mg of intermediate (17).

d) Preparation of

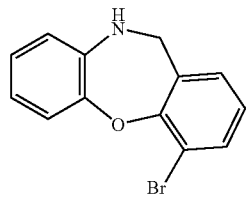
intermediate (18)

A mixture of intermediate (17) (17.9 mmol) and LiAlH$_4$ (89.6 mmol) in dioxane (200 mL) was stirred and refluxed for 5 hours. The reaction mixture was cooled on ice. Carefully, 3.5 mL water was added, the 3.5 mL 15% aqueous sodium hydroxide, then 10.5 mL water. The mixture was stirred at room temperature overnight, filtered and concentrated in vacuo. The residue was purified via RP HPLC, method A, yielding 750 mg of intermediate (18).

e) Preparation of

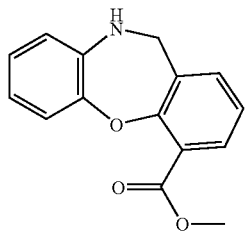
intermediate (19)

A 75-mL stainless steal autoclave was charged under nitrogen atmosphere with intermediate (18) (2.626 mmol), Pd(OAc)$_2$ (10 mg), 1.3 bis(diphenylphosphino)-propane (40 mg), potassium acetate (0.7 g), methanol (20 mL) and THF (20 mL). The autoclave was closed and pressurized to 50 bar carbonmonoxide and the reaction was carried out for 16 hours at a temperature of 125° C. The reaction mixture was filtered and concentrated in vacuo. The residue was partitioned between CH$_2$Cl$_2$ and water. The organic layer was dried on MgSO$_4$ and conc. The residue was purified by silica gel column chromatography (eluent heptane/CH$_2$Cl$_2$ 70/30 to 0/100), yielding 550 mg of intermediate (19) as a light yellow oil.

Example A.6

Preparation of

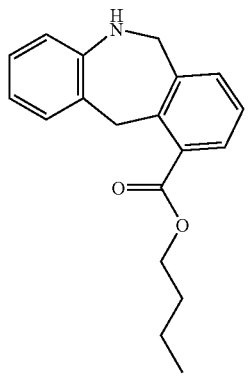
intermediate (20)

A 75-mL stainless steal autoclave was charged under nitrogen atmosphere with intermediate (3) (6 mmol), Pd(OAc)$_2$ (10 mg), 1.3 bis(diphenylphosphino)propane (40 mg), potassium acetate (1.5 g), n-butanol (20 mL) and THF (20 mL). The autoclave was closed and pressurized to 50 bar carbonmonoxide and the reaction was carried out for 16 hours at a temperature of 125° C. The reaction mixture was filtered and concentrated in vacuo. The residue was partitioned between CH$_2$Cl$_2$ and water. The separated organic layer was dried over MgSO$_4$, filtered and the filtrate was concentrated. The residue was purified by column chromatography over silica gel (eluent: heptane/EtOAc 100/0 to 80/20). The product fractions were collected and the solvent was evaporated, yielding 760 mg of intermediate (20).

Example A.7 a) Preparation of

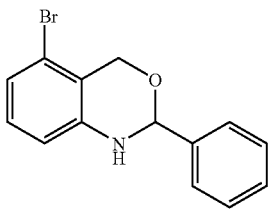

intermediate (24)

A mixture of 2-amino-6-bromo-benzenemethanol (35 mmol) and benzaldehyde (37 mmol) in 2-propanol (120 mL) was stirred overnight at room temperature. The solvent was evaporated, yielding intermediate (24).

b) Preparation of

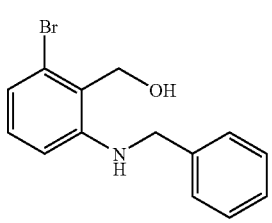

intermediate (25)

Reaction under nitrogen atmosphere. Sodium borohydride (70 mmol) was added slowly to a mixture of intermediate (24) (35 mmol) in ethanol (200 mL). The reaction mixture was stirred and refluxed for 2 hours. The mixture was cooled on an ice-water bath, quenched with NH$_4$Cl 20% (200 mL) followed by water (200 mL). The precipitate was filtered off and dried, yielding 9.2 g of intermediate (25).

c) Preparation of

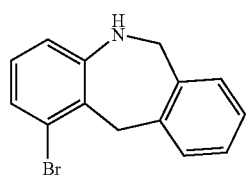

intermediate (26)

A H$_2$SO$_4$ solution (80 mL) was cooled to −10° C. on an ice-salt bath. A solution of intermediate (25) (31 mmol) in DCM (60 mL) was added dropwise. The ice-bath was removed, and stirring continued for 90 minutes at room temperature. The reaction mixture was cooled again, and a potassium hydroxide solution (10 M) was added carefully dropwise till the pH became basic. A precipitate was filtered off and washed with DCM and the aqueous filtrate was extracted with DCM (twice 300 mL). The organic layers were combined, dried (MgSO$_4$) and concentrated under reduced pressure, yielding 8.4 g of intermediate (26).

d) Preparation of

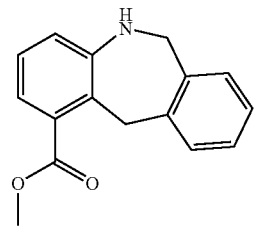

intermediate (27)

A mixture of intermediate (26) (7.3 mmol), Pd(OAc)$_2$ (0.15 mmol), potassium acetate (22 mmol) and 1,1'-(1,3-propanediyl)bis[1,1-d]phenyl-phosphine (0.29 mmol) in methanol (20 mL) and THF (20 mL) was reacted in a pressure reactor at 125° C. for 16 hours at 50 bar CO. The reaction mixture was cooled and filtered over dicalite, then concentrated in vacuo. The residue was partitioned between CH$_2$Cl$_2$ and water. The organic layer was dried over MgSO$_4$, filtered, then the filtrate was concentrated. The residue was purified by column chromatography over silica gel (eluent: CH$_2$Cl$_2$). The desired fractions were collected and the solvent was evaporated, yielding 1.54 g of intermediate (27).

Example A.8 a) Preparation of

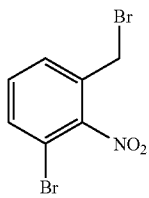

intermediate (28)

1-Bromo-3-methyl-2-nitro-benzene (46.29 mmol), dibenzoyl peroxide (250 mg), tetrachloromethane (100 ml) and 1-bromo-2,5-pyrrolidinedione (46.29 mmol) were refluxed overnight. Extra dibenzoyl peroxide (250 mg) was added and refluxing continued overnight. The reaction mixture was concentrated in vacuo and the residue partitioned between EtOAc and water. The organic layer was washed with water and brine, dried on MgSO$_4$ and concentrated, yielding 15 g of intermediate (28). The residue was used as such in the next step.

b) Preparation of

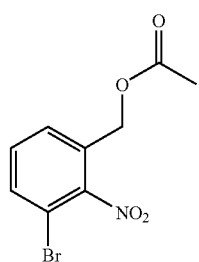

intermediate (29)

Intermediate (28) (46 mmol) and potassium acetate (322 mmol) in DMF (200 ml) were stirred at 70° C. for 2 hours. The reaction mixture was cooled and poured onto icewater, extracted twice with 300 mL EtOAc. The organic layer was washed with water and brine, dried on MgSO₄ and concentrated under reduced pressure. The residue was purified via SiO₂ column chromatography (eluent heptane/EtOAc 90/10 to 60/40). The pure fractions were collected and the solvent was evaporated, yielding 5.9 g of intermediate (29).

c) Preparation of

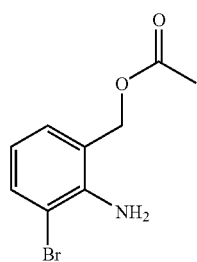

intermediate (30)

Pt/C₅% (1 g)+V₂O₅ (50 mg was suspended in THF under nitrogen flow. A 4% thiophene solution (0.5 ml) was added. Intermediate (29) (21.2 mmol) was added. The reaction mixture was stirred under hydrogen atmosphere until 3 equivalents hydrogen were absorbed. The catalyst was removed by filtration over dicalite. The mixture was concentrated, yielding 5.2 g of intermediate (30) that was used as such in the next step.

d) Preparation of

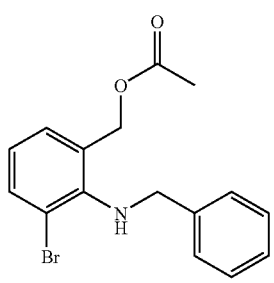

intermediate (31)

Intermediate (30) (6.8 mmol), benzyl bromide (7.4 mmol), sodium iodide (7.4 mmol) in DMF (50 ml) were stirred at 80° C. for 6 hours. The reaction mixture was cooled and water (500 mL) was added. The mixture was extracted twice with 250 mL EtOAc. The combined organic layer was washed with water and brine, dried on MgSO₄, and concentrated in vacuo. The residue was purified using purification method C. The pure fractions were collected and the solvent was evaporated, yielding intermediate (31).

e) Preparation of

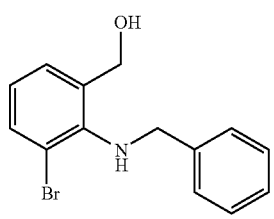

intermediate (32)

Intermediate (31) (5.7 mmol), methanol (20 mL) and sodium methylate in methanol (30%, 10 ml) were heated in a microwave at 160° C. for 20 minutes. The reaction mixture was concentrated under reduced pressure, and the residue was partitioned between DCM and water. The organic layer was dried on MgSO₄, concentrated under reduced pressure, yielding 1.7 g of intermediate (32) that was used as such in the next step.

f) Preparation of

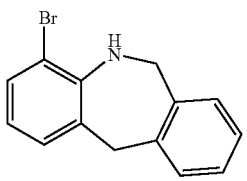

intermediate (33)

Sulfuric acid (25 mL) was cooled to −10° C. on an ice-salt bath. Then intermediate (32) (5.8 mmol) in DCM (20 mL) was added dropwise. The ice-bath was removed, and stirring continued for 1.5 hours at room temperature. The reaction mixture was cooled again, and KOH (10M) solution was added carefully dropwise till the pH became basic. The formed salt was filtered off and washed with DCM. The aqueous filtrate was extracted with DCM (2×300 mL). The combined organic layer was dried on MgSO₄ and concentrated under reduced pressure, yielding 1.36 g of intermediate (33).

g) Preparation of

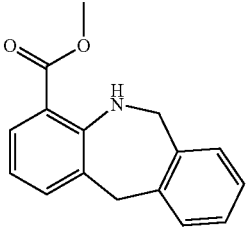

intermediate (34)

A 75-ml stainless steal autoclave was charged under nitrogen atmosphere with intermediate (33) (3.1 mmol), Pd(OAc)₂ (0.063 mmol), 1.3 bis(diphenylphosphino)-propane and potassium acetate (6.3 mmol) in methanol (20 mL) and THF (20 mL). The autoclave was closed and pressurized to 50 bar CO and the reaction was carried out for 16 hours at a temperature of 125° C. The reaction mixture was filtered over dicalite, concentrated in vacuo, and the residue was partitioned between saturated aqueous NaHCO₃ and DCM. The organic layer was dried on MgSO₄ and concentrated, yielding 545 mg of intermediate (34).

Example A.9 a) Preparation of

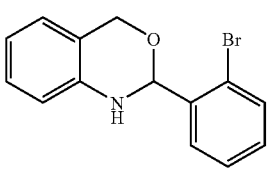

intermediate (35)

2-Amino-benzenemethanol (40.6 mmol) and 2-bromo-benzaldehyde (40.6 mmol) in isopropanol (60 mL) were stirred at room temperature overnight. The reaction mixture was concentrated in vacuo and the residue was used as such in the next step, yielding intermediate (35).

b) Preparation of

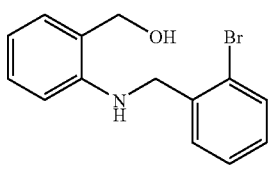

intermediate (36)

Under a nitrogen atmosphere, sodium tetrahydroborate (80 mmol) was added portionwise to intermediate (35) (40 mmol) in ethanol (120 mL). The mixture was stirred at reflux for 1 hour, cooled on an ice-bath and quenched with 20% aqueous NH$_4$Cl. The aqueous layer was extracted with DCM (2×250 mL). The organic layer was dried on MgSO$_4$, and concentrated in vacuo, yielding 11.7 g of intermediate (36).

c) Preparation of

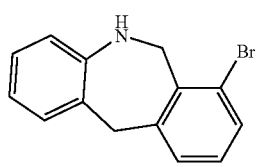

intermediate (37)

Sulfuric acid (100 mL) was cooled to −10° C. on an ice-salt bath. Then intermediate (36) (40 mmol) was added portionwise. The ice-bath was removed, and stirring continued for 1.5 hour at room temperature. The reaction mixture was cooled again, and an aqueous potassium hydroxide solution (10M) was added carefully dropwise till the pH became basic. The formed salt was filtered off and washed with diethylether. The aqueous filtrate was extracted twice with 300 mL diethylether. The combined organic layer was dried on MgSO$_4$ and concentrated under reduced pressure to yield a first residue. The formed salt before extraction was stirred with DCM, and filtered again. The organic layer was dried, concentrated under reduced pressure, and combined with the first residue. The combined residues were purified via column chromatography over silica gel (combiflash, eluent heptane/EtOAc 96/4 to 70/30). The pure fractions were collected and the solvent was evaporated, yielding 5.4 g of intermediate (37).

d) Preparation of

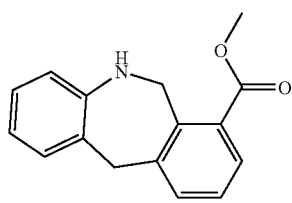

intermediate (38)

A 75-ml stainless steal autoclave was charged under nitrogen atmosphere with intermediate (37) (7.1 mmol), Pd(OAc)$_2$ (10 mg), (1.3 bis(diphenylphosphino)-propane (40 mg) and potassium acetate (1.5 g) in methanol (20 ml) and THF (20 ml). The autoclave was closed and pressurized to 50 bar CO and the reaction was carried out for 16 hours at a temperature of 125° C. The reaction mixture was filtered and concentrated in vacuo. The residue was partitioned between DCM and water. The organic layer was dried on MgSO$_4$ and concentrated. The residue was purified over column chromatography over silica gel (eluent DCM). The pure fractions were collected and the solvent was evaporated, yielding 1.520 g of intermediate (38).

Example A.10 a) Preparation of

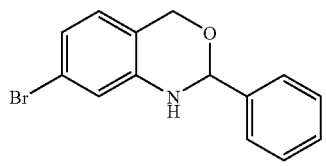

intermediate (39)

2-Amino-4-bromo-benzenemethanol (37.12 mmol) and benzaldehyde (40.83 mmol) in isopropanol (120 mL) were stirred at room temperature overnight. The reaction mixture was heated to 80° C. for 1 hour (clear solution), then slowly cooled to room temperature. The mixture was concentrated in vacuo, and toluene (120 mL) was added. The reaction mixture was refluxed under Dean-Strak conditions for 3 hours. The reaction mixture was concentrated under reduced pressure, and the residue was used as such in the next step, yielding intermediate (39).

b) Preparation of

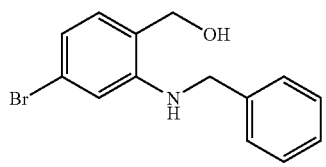

intermediate (40)

Under a nitrogen atmosphere, sodium tetrahydroborate (74 mmol) was added portionwise to intermediate (39) (37 mmol) in ethanol (120 ml). The mixture was stirred at reflux for 1 hour, cooled on an ice-bath and quenched with 20% aqueous NH$_4$Cl. The aqueous layer was extracted with DCM (2×250 mL). The organic layer was dried on MgSO$_4$, and concentrated in vacuo, yielding 10.8 g that was used as such in the next step.

c) Preparation of

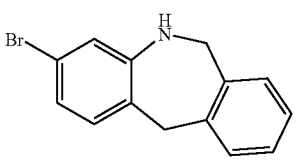

intermediate (41)

Sulfuric acid (100 mL) was cooled to −10° C. on an ice-salt bath. Then intermediate (40) (37 mmol) in DCM (30 mL) was added portionwise. The ice-bath was removed, and stirring continued for 1.5 hour at room temperature. The reaction mixture was cooled again, and an aqueous potassium hydroxide solution (10M) was added carefully dropwise till the pH became basic. To the salt mixture DCM (500 mL) was added and the mixture was stirred for 1 hour at room temperature. The salts were filtered off and washed with DCM. The combined organic layer was dried on MgSO$_4$ and concentrated under reduced pressure. The residue was purified by column chromatography over silica gel (combiflash, eluent DCM/heptane/EtOAc 10/86/4 to 7/63/30). The pure fractions werew collected and the solvent was evaporated, yielding, 6.4 g of intermediate (41) as a white solid.

d) Preparation of

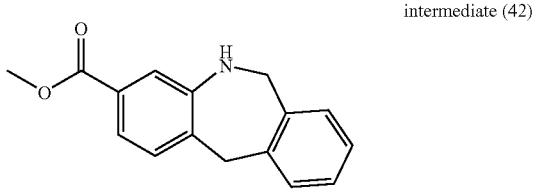 [SMILES: COC(=O)c1ccc2c(c1)NCc1ccccc1C2]

intermediate (42)

A 75-ml stainless steal autoclave was charged under nitrogen atmosphere with intermediate (41) (7.3 mmol), Pd(OAc)$_2$ (10 mg), 1.3 bis(diphenylphosphino)-propane (40 mg), potassium acetate (1.5 g) in methanol (20 mL) and THF (20 mL). The autoclave was closed and pressurized to 50 bar CO and the reaction was carried out for 16 hours at a temperature of 125° C. The reaction mixture was filtered and concentrated in vacuo. The residue was partitioned between DCM and water. The organic layer was dried on MgSO$_4$ and concentrated. The residue was purified by column chromatography over silica gel (eluent heptane/DCM 50/50 to 0/100). The pure fractions were collected and the solvent was evaporated, yielding 1.1 g of intermediate (42).

Example A.11 a) Preparation of

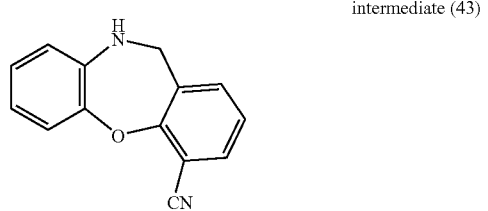 [SMILES: N#Cc1cccc2c1Oc1ccccc1NC2]

intermediate (43)

Intermediate (18) (2.7 mmol) and copper cyanide (6.8 mmol) in DMF (15 mL) were degassed and then shaken under nitrogen atmosphere at 140° C. overnight. The reaction mixture was cooled to room temperature and sodium hydroxide (200 mL, 0.2N) was added. The mixture was extracted twice with 100 mL EtOAc. The combined organic layer was washed with water and brine and dried on MgSO$_4$ and concentrated in vacuo, yielding 255 mg of intermediate (43).

b) Preparation of

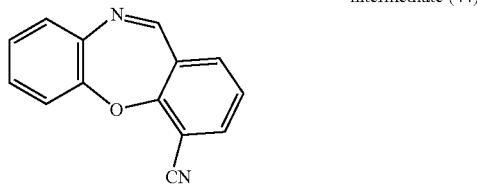

intermediate (44)

Intermediate (43) (1.125 mmol) and manganese oxide (3.375 mmol) in toluene (15 mL) were stirred at 80° C. for 3 hours. The reaction mixture was filtered over a dicalite pad, eluent toluene, then DCM. The DCM layer was concentrated and purified using purification method C, yielding 90 mg of intermediate (44).

Example A.12 a) Preparation of

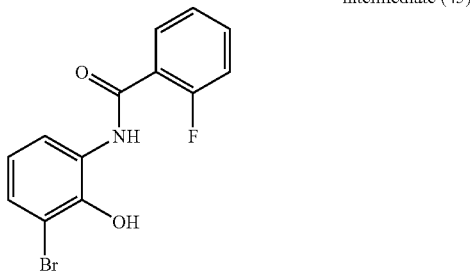

intermediate (45)

2-Fluoro-benzoyl chloride (15.6 mmol) in THF (25 mL) was added dropwise to a mixture of 2-amino-6-bromo-phenol (15.6 mmol) and triethylamine (31.1 mmol) in THF (75 mL) at 0° C. The reaction mixture was allowed to warm to room temperature and stirred overnight. The reaction mixture was poured into water (400 mL) and acidified to pH 4-5 with 1N aqueous HCl. The aqueous layer was extracted twice with 200 ml, of DCM. The organic layer was dried on MgSO$_4$ and concentrated in vacuo. The residue was purified using purification method A, yielding 2.8 g of intermediate (45).

b) Preparation of

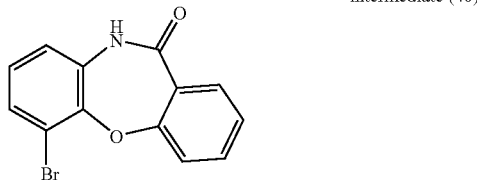

intermediate (46)

Intermediate (45) (8.9 mmol) and sodium hydroxide (powder, 8.9 mmol) in DMF (60 mL) were refluxed for 5 hours. The reaction mixture was poured onto ice water (800 mL) and the resulting precipitate filtered off and washed with 1N aqueous NaOH and water, then dried in vacuo, yielding intermediate (46).

c) Preparation of

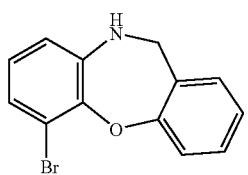

intermediate (47)

To a suspension of intermediate (46) (8.445 mmol) in THF (80 mL) was added borane 1M in THF (25.3 mmol) at room temperature. The reaction mixture was stirred further at room temperature over the weekend. The reaction mixture was cooled on ice and 100 ml, 1N aqueous HCl was added. The mixture was partly concentrated in vacuo, then basified with solid NaHCO$_3$ (pH about 7). The aqueous layer was extracted twice with 150 mL DCM. The organic layer was dried on MgSO$_4$ and concentrated. The residue was purified using purification method A, yielding 1.350 g of intermediate (47).

d) Preparation of

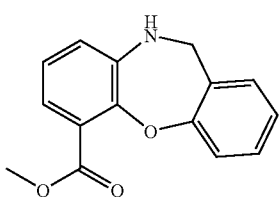

intermediate (48)

A 75-ml stainless steal autoclave was charged under nitrogen atmosphere with intermediate (47) (2.3 mmol), Pd(OAc)$_2$ (0.046 mmol), 1.3 bis(diphenylphosphino)-propane (0.093 mmol), potassium acetate (6.95 mmol) in methanol (20 mL) and THF (20 mL). The autoclave was closed and pressurized to 50 bar CO and the reaction was carried out for 16 hours at a temperature of 125° C. The reaction mixture was filtered over dicalite, concentrated in vacuo, and the residue was partitioned between saturated aqueous NaHCO$_3$ and DCM. The organic layer was dried on MgSO$_4$ and concentrated, yielding 550 mg of intermediate (48).

Example A.13 a) Preparation of

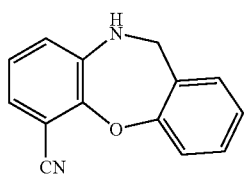

intermediate (49)

Intermediate (47) (2.716 mmol), copper cyanide (6.79 mmol) were degassed and then shaken under nitrogen at 140° C. overnight. The reaction mixture was cooled to room temperature and an aqueous NaOH solution (200 mL, 0.2N) was added. The mixture was extracted twice with 100 mL EtOAc. The combined organic layer was washed with water and brine and dried on MgSO$_4$, concentrated in vacuo, yielding 500 mg of intermediate (49), which was used as such in the next step.

b) Preparation of

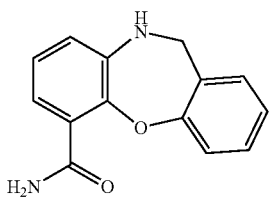

intermediate (50)

Intermediate (49) (2.25 mmol) in sulfuric acid (3 mL) was stirred at room temperature overnight and then stirred another 2 days at room temperature. The reaction mixture was poured on 100 mL icewater and basified with aqueous NH$_3$ solution and then extracted twice with 100 mL DCM. The combined organic layer was washed with brine, dried on MgSO$_4$ and concentrated, yielding 510 mg of intermediate (50).

B. Preparation of the Final Compounds

Example B.1

Preparation of

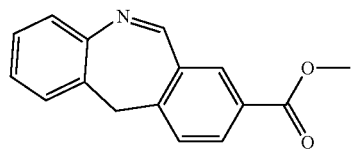

compound (1)

A mixture of intermediate (3) (0.010 mol), 1,1'-(1,3-propanediyl)bis[1,1-d]phenyl-phosphine (0.08 g), Pd(OAc)$_2$ (0.02 g) and triethylamine (3 g) in methanol (50 mL) and THF (50 mL) was stirred in an autoclave at 125° C. for 16 hours under 50 atmosphere of CO pressure, then for 4 hours at 150° C. The reaction mixture was cooled and filtered over dicalite. The filtrate's solvent was evaporated The residue was purified via reversed phase HPLC (method B). The desired fraction was collected and the solvent was evaporated, yielding 380 mg of compound (1).

Example B.2

Preparation of

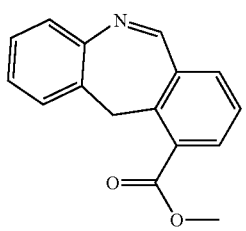

compound (2)

A mixture of intermediate (5) (0.00735 mol) and manganese oxide (0.0367 mol) in toluene (20 mL) was stirred at 90° C. for 4 hours. The reaction mixture was filtered over a silica gel pad (eluent: toluene, then CH$_2$Cl$_2$). The (yellow) CH$_2$Cl$_2$ layer was concentrated. The residue was purified by column chromatography over silica gel (eluent: heptane/EtOAc 100/0 to 70/30). The product fractions were collected and the solvent was evaporated. The residue was triturated under DIPE, filtered off and dried, yielding 1.35 g of compound (2).

Example B.3

Preparation of

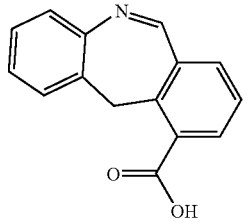
compound (4)

A mixture of intermediate (5) (0.001 mol) in THF (30 mL) and LiOH (1N aqueous solution, 10 mL) was stirred at room temperature for 2 hours. The reaction mixture was heated overnight at 50° C., then allowed to stand over the weekend at room temperature. The mixture was concentrated in vacuo. The residue was purified via reversed phase HPLC (method A), yielding 0.100 g of compound (4).

Example B.4

Preparation of

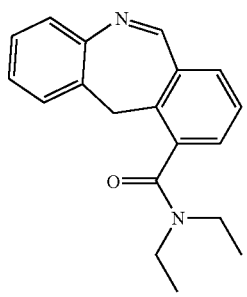
compound (5)

Heck reaction with CO insertion. A mixture of intermediate (4) (0.003 mol), N-ethyl-ethanamine (1 g), Pd(OAc)$_2$ (0.010 g) and 1,1'-(1,3-propanediyl)bis[1,1-d]phenyl-phosphine (0.040 g) in THF (50 mL) was reacted in a pressure reactor at 150° C. for 16 hours under 50 atmosphere of CO pressure. The reaction mixture was filtrated through dicalite and the filtrate was concentrated. The residue was purified by reversed phase HPLC (method A). The desired fraction was collected and the solvent was evaporated, yielding 0.006 g of compound (5).

Example B.5

Preparation of

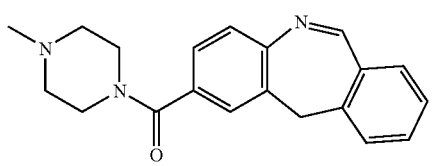
compound (8)

A mixture of intermediate (7) (1,58 mg) in DMSO (0.49 mL) was stored at room temperature for about 6 months, yielding 0.71 mg of compound (8) as a solution in DMSO.

Example B.6

Preparation of

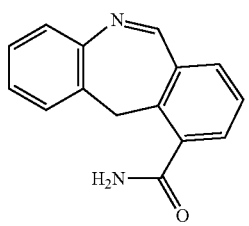
compound (9)

Intermediate (9) and sulfuric acid were stirred at a temperature between 0 and 5° C. for 2 hours. The mixture was kept stirring at room temperature for 4 days. The reaction mixture was poured on 50 mL ice water, and basified with a concentrated aqueous NH$_3$ solution. The formed precipitate was filtered off, dissolved in methanol and concentrated. The residue was purified via RP HPLC (method A) to give compound (9).

Example B.7

Preparation of

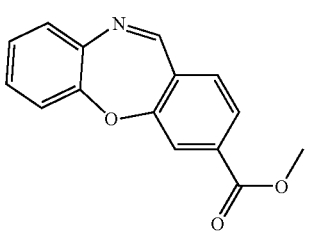
compound (10)

A mixture of intermediate (14) (3.016 mmol) and manganese oxide (9.049 mmol) in toluene (20 mL) was stirred at 80° C. for 3 hours. The reaction mixture was filtered over a dicalite pad (eluent toluene, then CH$_2$Cl$_2$), and purified by silica gel chromatography (eluent: heptane/EtOAc 100/0 to 50/50), to give one pure fraction, which was after concentration in vacuo, solidified from DIPE, filtered off and dried, yielding 50 mg of compound (10).

Example B.8

Preparation of

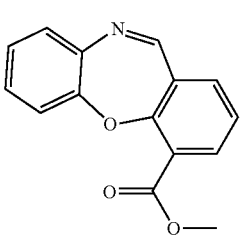
compound (11)

A mixture of intermediate 19 (1.998 mmol) and manganese oxide (5.994 mmol) in toluene (20 mL) was stirred at 80° C. for 3 hours. The reaction mixture was filtered over a dicalite pad (eluent toluene, then $CH_2Cl_2$). The (yellow) $CH_2Cl_2$ layer was concentrated and purified by silica gel chromatography (eluent $CH_2Cl_2/CH_3OH(NH_3)$ 100/0 to 99/1). The pure fractions were collected and the solvent was evaporated, yielding 440 mg of compound (11).

Example B.9

Preparation of compound (13)

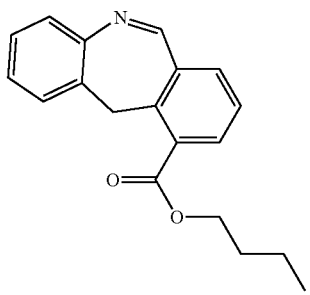

and compound (14)

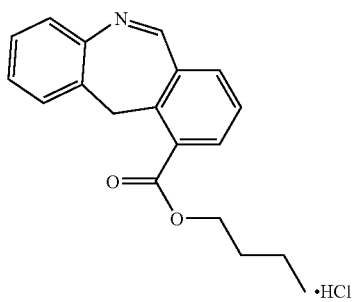

A mixture of intermediate (20) (2.404 mmol) and manganese oxide (7.211 mmol) in toluene (20 mL) was stirred at 80° C. for 3 hours. The reaction mixture was filtered over a dicalite pad, eluent toluene, then $CH_2Cl_2$. The $CH_2Cl_2$ layer was concentrated and purified by silica gel chromatography (eluent $CH_2Cl_2/CH_3OH(NH_3)$ 100/0 to 99/1). The pure fractions were collected and the solvent was evaporated, yielding 630 mg of compound (13).

A part (587 mg) of compound (13) was dissolved in diethyl ether (12 mL) and 1 mL 2N HCl in diethyl ether was added. The resulting sticky material was dissolved by adding 1.5 mL of $CH_3CN$. Then 1.5 mL of diisopropylether was added, after which the product crystallized. The solid was filtered off and washed with diisopropylether and dried in vacuo, yielding 616 mg of compound (14).

Example B.10

Preparation of compound (15)

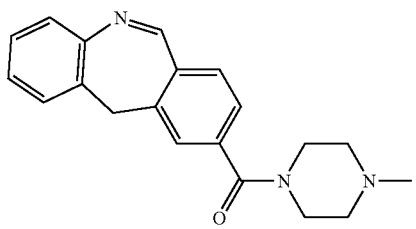

A mixture of intermediate (22) (0.00492 mmol) in DMSO (0.7 mL) was stored at room temperature for about 6 months, yielding 0.45 mg of compound (15) as a solution in DMSO.

Example B.11

Preparation of compound (16)

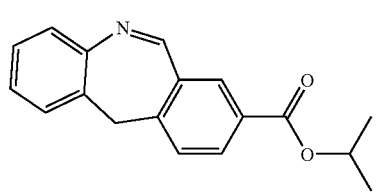

A mixture of intermediate (23) (1.15 mmol) and manganese oxide (3.451 mmol) in toluene (15 mL) was stirred at 80° C. for 3 hours. The reaction mixture was filtered over a dicalite pad, eluent toluene, then $CH_2Cl_2$. The $CH_2Cl_2$ layer was concentrated and purified by silica gel chromatography (eluent: $CH_2Cl_2$). The pure fractions were collected and the solvent was evaporated. The residue was purified further via reversed phase HPLC (method A), yielding 40 mg of compound (16).

Example B.12

Preparation of compound (21)

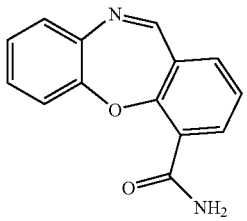

A mixture of intermediate (44) (0.272 mmol) in $H_2SO_4$ (2 mL) was stirred for two days. The reaction mixture was poured on water (100 mL) and basified with an aqueous $NH_3$ solution. This mixture was extracted with DCM (twice 200 mL). The combined organic layers were washed with brine, dried ($MgSO_4$) and concentrated, yielding compound (21).

Table 1 lists the compounds that were prepared according to one of the above Examples.
TABLE 1
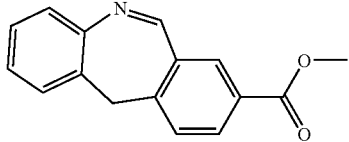
Co. No. 1; Ex. B.1
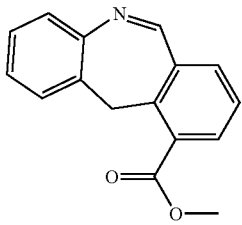
Co. No. 2; Ex. B.2
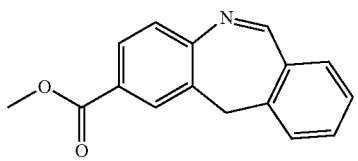
Co. No. 3; Ex. B.2
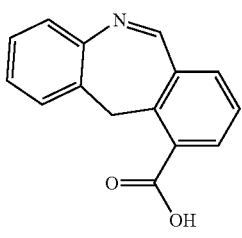
Co. No. 4; Ex. B.3
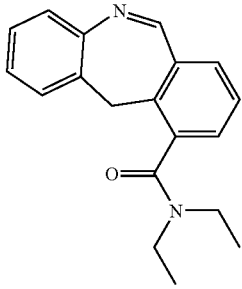
Co. No. 5; Ex. B.4
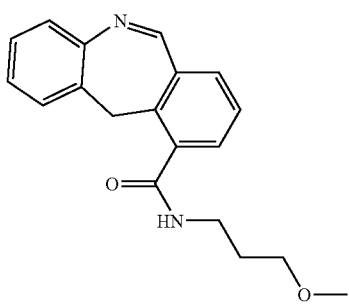
Co. No. 6; Ex. B.4
TABLE 1-continued
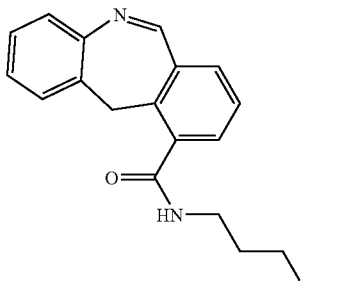
Co. No. 7; Ex. B.4
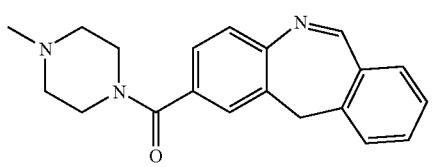
Co. No. 8; Ex. B.5
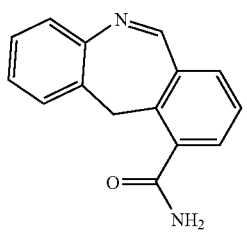
Co. No. 9; Ex. B.6
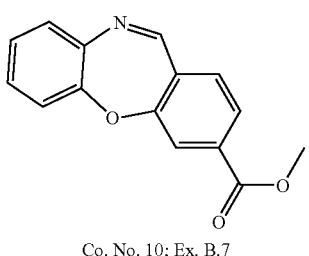 [SMILES: COC(=O)c1ccc2c(c1)Oc1ccccc1N=C2]
Co. No. 10; Ex. B.7
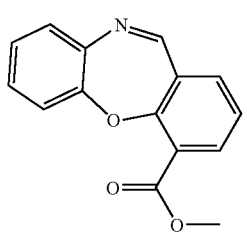
Co. No. 11; Ex. B.8
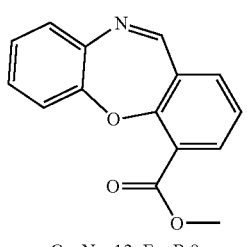
Co. No. 12; Ex. B.8

TABLE 1-continued
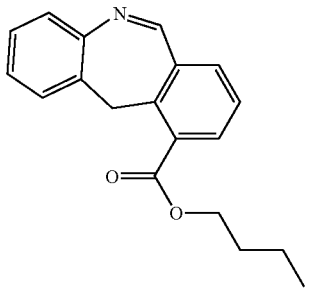
Co. No. 13; Ex. B.9
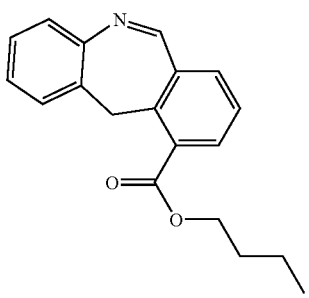
Co. No. 14; Ex. B.9
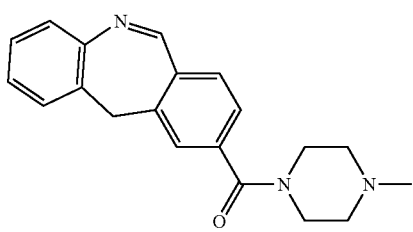
Co. No. 15; Ex. B.10
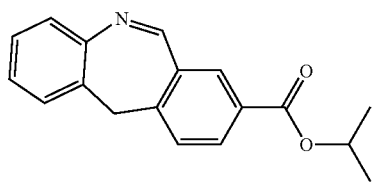
Co. No. 16; Ex. B.11
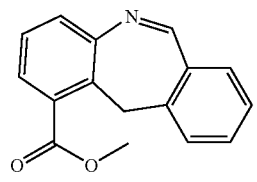
Co. No. 17; Ex. B.2
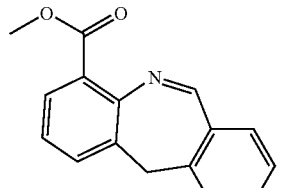
Co. No. 18; Ex. B.2
TABLE 1-continued
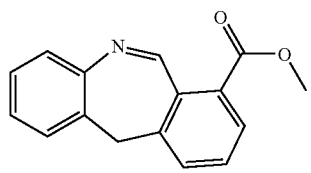
Co. No. 19; Ex. B.2
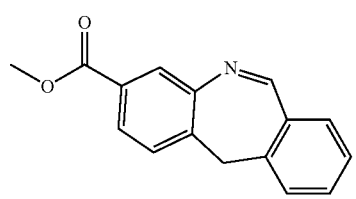
Co. No. 20; Ex. B.2
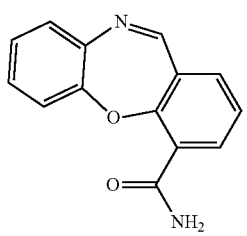
Co. No. 21; Ex. B.12
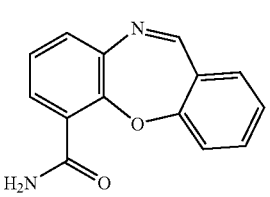
Co. No. 22; Ex. B.2
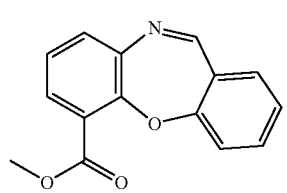
Co. No. 23; Ex. B.2
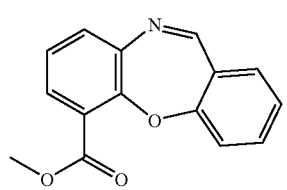
Co. No. 24; Ex. B.2; •HCl
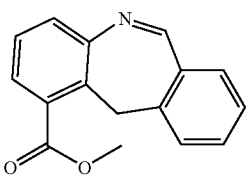
Co. No. 25; Ex. B.2; •HCl TABLE 1-continued

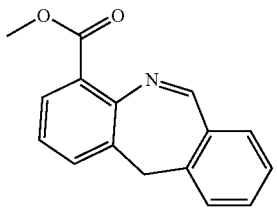

Co. No. 26; Ex. B.2; ·HCl

C. Analytical Part
C.1. LC-MS General Procedure 1

The LC measurement was performed using an Acquity HPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

Reversed phase HPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (mobile phase A: 0.1% formic acid in $H_2O$/methanol 95/5; mobile phase B: methanol) were used to run a gradient condition from 95% A and 5% B to 5% A and 95% B in 1.3 minutes and hold for 0.2 minutes. An injection volume of 0.5 μl was used. Cone voltage was 10 V for positive ionization mode and 20 V for negative ionization mode.

C.2. LC-MS General Procedure 2 The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

Column heater was set at 45° C. Reversed phase HPLC was carried out on an Xterra MS C18 column (3.5 μm, 4.6×100 mm) with a flow rate of 1.6 ml/min. Three mobile phases (mobile phase A: 0.1% formic acid in $H_2O$/methanol 95/5; mobile phase B: acetonitrile; mobile phase C: methanol) were employed to run a gradient condition from 100% A to 1% A, 49% B and 50% C in 7 minutes and hold these conditions for 1 minute. An injection volume of 10 μl was used. Cone voltage was 10 V for positive ionization mode.

C.3 Melting Points

For a number of compounds, melting points (m.p.) were determined with a DSC823e (Mettler-Toledo). Melting points were measured with a temperature gradient of 30° C./minute. The reported values are peak values. Maximum temperature was 400° C. Values are obtained with experimental uncertainties that are commonly associated with this analytical method.

TABLE 2

Analytical data - Retention time ($R_t$ in minutes), (MH)+ peak (of the free base), LC-MS procedure and melting points (m.p. is defined as melting point).

| Co. Nr. | $R_t$ | (MH)+ | LC-MS Procedure | m.p. (° C.) |
|---|---|---|---|---|
| 1 | — | — | — | 137.9 |
| 2 | 1.17 | 252 | 1 | — |
| 3 | 1.18 | 252 | 1 | 111.9 |
| 4 | 0.93 | 238 | 1 | — |
| 5 | 1.09 | 293 | 1 | — |
| 6 | 0.93 | 309 | 1 | — |
| 7 | 0.92 | 309 | 1 | — |
| 8 | 0.63 | 320 | 1 | — |
| 9 | 0.66 | 237 | 1 | — |
| 10 | 1.24 | 254 | 1 | 105.4 |
| 11 | 1.16 | 254 | 1 | 205.5 |
| 12 | 1.16 | 254 | 1 | — |
| 13 | 1.43 | 294 | 1 | — |
| 14 | 1.43 | 294 | 1 | 173.0 |
| 15 | 0.57 | 320 | 1 | — |
| 16 | 1.34 | 280 | 1 | — |
| 17 | 1.21 | 252 | 1 | 89.9 |
| 18 | 1.2 | 252 | 1 | — |
| 19 | 1.17 | 252 | 1 | 123.9 |
| 20 | 5.39 | 252 | 2 | 106.0 |
| 21 | 0.83 | 239 | 1 | 193.0 |
| 22 | 0.84 | 239 | 1 | 193.2 |
| 23 | 1.2 | 254 | 1 | — |
| 24 | 1.2 | 254 | 1 | — |
| 25 | 1.21 | 252 | 1 | — |
| 26 | 1.2 | 252 | 1 | — |

D. Pharmacological Examples
Cell and Culture

The Human TRPA1 gene was cloned into the pT-REx-Dest30 inducible vector and afterwards stably transfected in T-Rex™-293 cells (purchased from Invitrogen, Merelbeke, Belgium). This tetracyclin inducible hTRPA1 expression system was used in order to prevent $Ca^{2+}$ overload in the cultured cells due to sustained TRPA1 expression. hTRPA1/TREx-HEK293 cells (referred to as hTRPA1 cells in the following text) were maintained under standard sterile cell culture conditions. The culture medium for the hTRPA1-HEK cells was DMEM (Gibco BRL, Invitrogen, Merelbeke, Belgium) supplemented with 0.5 g/l geneticin (Gibco), 5 mg/l blasticidin (Invitrogen), 14.6 g/l L-Glutamine (200 mM; Gibco), 5 g/l penicillin/streptomycin ($5.10^{-6}$ IU/l, Gibco), 5.5 g/l pyruvic acid (Gibco) and 10% foetal calf serum (Hyclone, Logan Utah, USA).

$Ca^{2+}$Fluorometry

Binding of an agonist to the TRPA1 ion-channel activates and opens the ion-channel which causes a robust increase in intracellular $Ca^{2+}$ concentration. For detecting and measuring intracellular $Ca^{2+}$ concentration, cells were loaded with a $Ca^{2+}$-sensitive dye. Changes in fluorescence in the cell, that correspond to changes in $Ca^{2+}$ concentration in the cell, can kinetically be monitored with the FDSS instrument (Hamamatsu) and are indicative for agonism towards the TRPA1 ion channel.

For the fluorometric $Ca^{2+}$ measurements hTRPA1-HEK cells were resuspended in HBSS seeding medium: HBSS (with $CaCl_2$ and $MgCl_2$; Gibco) supplemented with 14.6 g/l L-Glutamine (200 mM; Gibco), 5 g/l penicillin/streptomycin ($5.10^{-6}$ IU/l, Gibco), 5.5 g/l pyruvic acid (Gibco), 5 mM HEPES (Gibco), 5 ml Insulin-Transferrin-Xelenium-x (Gibco) and 10% foetal calf serum (heat inactivated for 30 minutes at 56° C.; Hyclone, Logan Utah, USA). The cells were seeded in poly-D-lysine-coated 384-well round bottom polypropylene plates (Costar Corning, Data Packaging, Cambridge Mass., USA) at 12000 cells/well. 50 ng/ml tetracycline was added to induce the hTRPA1 expression 24 h before the experiment.

The cells were loaded with 5 mg/l Fluo-4-AM (Molecular Probes, Invitrogen, Merelbeke, Belgium) dissolved in HBSS seeding medium supplemented with 0.7 g/l Probenecid (Sigma) and incubated for 1 h at 37° C. and subsequently at 20° C. for 1 to 2 h. The fluorescence was measured in the FDSS 6000 imaging based plate reader (Hamamutsu Photonics K.K., Hamamutsu City, Japan). The excitation wavelength was 488 nm and the emission wavelength 540 nm. After a control period of 12 seconds the compounds were added and the $Ca^{2+}$ signal was measured within 14 minutes after application.

TABLE 3 pEC50 values for TRPA1 agonism

| Co. No. | pEC50 |
| --- | --- |
| 1 | 7.03 |
| 2 | 10.00 |
| 3 | 9.24 |
| 4 | 6.44 |
| 5 | 7.35 |
| 6 | 8.06 |
| 7 | 8.23 |
| 8 | 8.50 |
| 9 | 8.60 |
| 10 | 7.28 |
| 11 | 10.09 |
| 12 | 10.22 |
| 13 | 8.07 |
| 14 | 8.25 |
| 15 | 5.79 |
| 16 | 6.03 |
| 17 | 9.24 |
| 18 | 7.56 |
| 19 | 7.54 |
| 20 | 7.55 |
| 21 | 10.12 |
| 22 | 9.94 |
| 23 | 9.93 |
| 24 | 10.13 |
| 25 | 9.35 |
| 26 | 7.42 |

The invention claimed is:

1. A compound of formula (I)

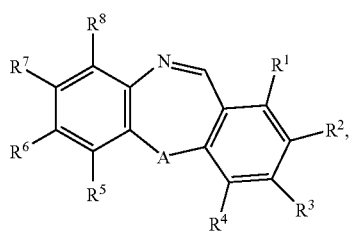

(I)

or any stereochemically isomeric form thereof wherein

A is $CH_2$, CO, or O;

$R^1, R^2, R^3, R^4, R^5, R^6, R^7$ and $R^8$ are each independently selected from hydrogen, halo, hydroxy, $C_{1-6}$alkyl, polyhalo$C_{1-6}$alkyl, $C_{3-6}$cycloalkyl, $C_{1-6}$alkyloxy, polyhalo$C_{1-6}$alkyloxy, COOR$^9$ or CONR$^{10}$R$^{11}$;

wherein $R^9, R^{10}$ and $R^{11}$ are each independently selected from hydrogen, $C_{1-6}$alkyl, $C_{1-4}$alkyloxy$C_{1-4}$alkyl, polyhalo$C_{1-6}$alkyl, polyhalo$C_{1-4}$alkyloxy$C_{1-4}$alkyl, $C_{3-6}$cycloalkyl, $C_{3-6}$cycloalkyl$C_{1-4}$alkyl, amino$C_{2-5}$alky, mono- or (di$C_{1-4}$alkyl)amino$C_{2-5}$alkyl; and wherein NR$^{10}$R$^{11}$ may form a heterocyclic ring selected from pyrrolidine, piperidine, morpholine, piperazine, or piperazine substituted with $C_{1-4}$alkyl;

provided that at least one of $R^1, R^2, R^3, R^4, R^5, R^6, R^7$ and $R^8$ is defined as COOR$^9$ or CONR$^{10}$R$^{11}$; and provided that when radical A represents O then the substituents $R^5, R^6, R^7$ and $R^8$ are not COOR$^9$;

or a pharmaceutically acceptable salt thereof, or an N-oxide thereof.

2. A compound as claimed in claim 1 wherein one of the substituents $R^1, R^2, R^3, R^4, R^5, R^6, R^7$ and $R^8$ is COOR$^9$, wherein $R^9$ is $C_{1-4}$alkyl.

3. A compound as claimed in claim 1 wherein one of the substituents $R^1, R^2, R^3, R^4, R^5, R^6, R^7$ and $R^8$ is COOR$^9$, wherein $R^9$ is $C_{1-4}$alkyl, and the other $R^1, R^2, R^3, R^4, R^5, R^6, R^7$ and $R^8$ substituents are hydrogen and A is $CH_2$, CO or O.

4. A compound as claimed in claim 1 wherein $R^4$ is COOR$^9$ wherein $R^9$ is $C_{1-4}$alkyl, and the substituents $R^1, R^2, R^3, R^5, R^6, R^7$ and $R^8$ are hydrogen and A is $CH_2$ or O, or $R^6$ is COOR$^9$ wherein $R^9$ is $C_{1-4}$alkyl, and the substituents $R^1, R^2, R^3, R^4, R^5, R^7$ and $R^8$ are hydrogen and A is $CH_2$, or $R^5$ is COOR$^9$ wherein $R^9$ is $C_{1-4}$alkyl, and the substituents $R^1, R^2, R^3, R^4, R^5, R^6, R^7$ and $R^8$ are hydrogen and A is $CH_2$.

5. A pharmaceutical composition comprising a pharmaceutically acceptable carrier and a therapeutically active amount of a compound of claim 1.

6. A process for preparing a pharmaceutical composition, wherein a therapeutically active amount of a compound of claim 1 is intimately mixed with a pharmaceutically acceptable carrier.

7. A compound of claim 1, wherein $R^1, R^2, R^3, R^4, R^5, R^6, R^7$ and $R^8$ are each independently selected from hydrogen or CONR$^{10}$R$^{11}$.

8. A compound of claim 7, wherein $R^{10}$ and $R^{11}$ are each hydrogen.

9. A compound of formula (I)

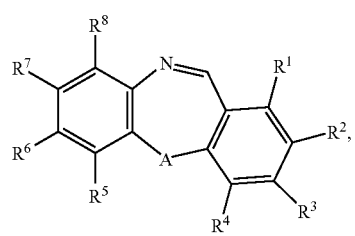

(I)

or any stereochemically isomeric form thereof wherein

A is $CH_2$, or O;

$R^1, R^2, R^3, R^4, R^5, R^6, R^7$ and $R^8$ are each independently selected from hydrogen, COOR$^9$ or CONR$^{10}$R$^{11}$;

wherein $R^9, R^{10}$ and $R^{11}$ are each independently selected from hydrogen, $C_{1-6}$alkyl or $C_{1-4}$alkyloxy$C_{1-4}$alkyl; and wherein NR$^{10}$R$^{11}$ may form a piperazine, or piperazine subsituted with $C_{1-4}$alkyl;

provided that at least one of $R^1$, $R^2$, $R^3$, $R^4$, $R^5$, $R^6$, $R^7$ and $R^8$ is defined as $COOR^9$ or $CONR^{10}R^{11}$; and provided that when radical A represents O then the substituents $R^5$, $R^6$, $R^7$ and $R^8$ are not $COOR^9$;

or a pharmaceutically acceptable salt thereof, or an N-oxide thereof.

10. A compound of claim 7, wherein $R^4$ is $CONR^{10}R^{11}$.

11. A compound selected from the group consisting of;

methyl 11H-dibenzo[b,e]azepine-8-carboxylate;
methyl 11H-dibenzo[b,e]azepine-10-carboxylate;
methyl 11H-dibenzo[b,e]azepine-2-carboxylate;
11H-dibenzo[b,e]azepine-10-carboxylic add;
N,N-diethyl-11H-dibenzo[b,e]azepine-10-carboxamide;
N-(3-methoxypropyl)-11H-dibenzo[b,e]azepine-10-carboxamide;
(11H-dibenzo[b,e]azepin-2-yl)(4-methylpiperazin-1-yl)methanone;
11H-dibenzo[b,e]azepine-10-carboxamide;
methyl dibenzo[b,f][1,4]oxazepine-3-carboxylate;
methyl dibenzo[b,f][1,4]oxazepine-4-carboxylate;
butyl 11H-dibenzo[b,e]azepine-10-carboxylate;
butyl 11H-dibenzo[b,e]azepine-10-carboxylate hydrochloride;
(11H-dibenzo[b,e]azepin-9-yl)(4-methylpiperazin-1-yl)methanone;
isopropyl 11H-dibenzo[b,e]azepine-8-carboxylate;
methyl 11H-dibenzo[b,e]azepine-1-carboxylate;
methyl 11H-dibenzo[b,e]azepine-4-carboxylate;
methyl 11H-dibenzo[b,e]azepine-7-carboxylate;
methyl 11H-dibenzo[b,e]azepine-3-carboxylate;
dibenzo[b,f][1,4]oxazepine-4-carboxamide;
dibenzo[b,f][1,4]oxazepine-6-carboxamide;
methyl 11H-dibenzo[b,e]azepine-1-carboxylate hydrochloride; and
methyl 11H-dibenzo[b,e]azepine-4-carboxylate hydrochloride.

* * * * *

UNITED STATES PATENT AND TRADEMARK OFFICE
CERTIFICATE OF CORRECTION

| | | |
|---|---|---|
| PATENT NO. | : 8,461,145 B2 | |
| APPLICATION NO. | : 12/746092 | |
| DATED | : June 11, 2013 | |
| INVENTOR(S) | : Gijsen et al. | |

It is certified that error appears in the above-identified patent and that said Letters Patent is hereby corrected as shown below:

In the Claims

Claim 11, in column 41, line 12 should read as follows:
11H-dibenzo[b,e]azepine-10-carboxylic acid;

Signed and Sealed this
Seventh Day of January, 2014

Margaret A. Focarino
*Commissioner for Patents of the United States Patent and Trademark Office*